United States Patent
Ziff et al.

(10) Patent No.: US 7,871,609 B2
(45) Date of Patent: Jan. 18, 2011

(54) SUPPLEMENTS FOR PAIN MANAGEMENT

(76) Inventors: Sam Ziff, 1617 E. Robinson St., Apt. 2, Orlando, FL (US) 32803; David Ziff, 1822 Hillcrest Dr., Orlando, FL (US) 32803

( * ) Notice: Subject to any disclaimer, the term of this patent is extended or adjusted under 35 U.S.C. 154(b) by 369 days.

(21) Appl. No.: 12/038,534

(22) Filed: Feb. 27, 2008

(65) Prior Publication Data
US 2008/0213246 A1 Sep. 4, 2008

Related U.S. Application Data

(60) Provisional application No. 60/904,710, filed on Mar. 2, 2007.

(51) Int. Cl.
*A61K 9/00* (2006.01)
*A61K 38/43* (2006.01)
*A61K 38/46* (2006.01)
*A61K 38/48* (2006.01)

(52) U.S. Cl. ............... 424/94.65; 424/94.63; 424/94.6; 424/94.1; 424/400

(58) Field of Classification Search ............... 424/94.65
See application file for complete search history.

(56) References Cited

U.S. PATENT DOCUMENTS

| | | | |
|---|---|---|---|
| 5,804,594 A | 9/1998 | Murad | |
| 5,885,597 A | 3/1999 | Botknecht et al. | |
| 5,925,377 A * | 7/1999 | Gerth et al. | ............ 424/451 |
| 6,210,701 B1 | 4/2001 | Darland et al. | |
| 6,352,712 B1 | 3/2002 | Lukaczer et al. | |
| 6,399,089 B1 * | 6/2002 | Yegorova et al. | ............ 424/439 |
| 6,534,086 B1 | 3/2003 | Krumhar | |
| 6,602,517 B2 | 8/2003 | Darland et al. | |
| 6,617,349 B2 | 9/2003 | Green et al. | |
| 6,949,260 B2 | 9/2005 | Krumhar | |
| 6,979,470 B2 | 12/2005 | Babish et al. | |
| 7,138,149 B2 | 11/2006 | Cho | |
| 2002/0051826 A1 | 5/2002 | Darland | |
| 2003/0068383 A1 | 4/2003 | Patterson et al. | |
| 2004/0028675 A1 | 2/2004 | Ziegler | |
| 2004/0052873 A1 | 3/2004 | Qazi et al. | |
| 2004/0086581 A1 | 5/2004 | Jones | |
| 2004/0121028 A1 | 6/2004 | Qazi et al. | |
| 2004/0247700 A1 | 12/2004 | Babish et al. | |
| 2005/0265990 A1 | 12/2005 | Talbott | |
| 2005/0282772 A1 * | 12/2005 | Gokaraju et al. | ............ 514/54 |
| 2006/0040000 A1 | 2/2006 | Gokaraju et al. | |
| 2006/0240037 A1 | 10/2006 | Fey et al. | |
| 2006/0246115 A1 | 11/2006 | Rueda et al. | |

OTHER PUBLICATIONS

Jurna I, Schmerz, Analgetische und analgesie-potenzietende Wirkung von B-Vitaminen, Medizinische Fakultat der Universitat des Saarlandes, Apr. 20, 1998, pp. 136-141, vol. 12, No. 2.
Gokhale, Leela B., Curative treatment of primary (spasmodic) dysmenorrhoea, Indian J. Med. Res., Apr. 1996, pp. 227-231, vol. 103.
Kandarkar, et al., Subchronic oral heptotoxicity of turmeric in mice—Histopathological and ultrastructural studies, Indian Journal of Experimental Biology, Jul. 1998, pp. 675-679, vol. 36.
Bender, David A., Novel functions of vitamin B6, Proceedings of the Nutrition Society, 1994, pp. 625-630, vol. 53.
Chandra, et al., Regulation of Immune Responses by Vitamin B6, NY Acad Sci, 1990, pp. 404-423, vol. 585.
Trakatellis, et al., Pyridoxine deficiency: new approaches in immunosuppression and chemotherapy, Postgrad Med J, 1997; pp. 617-622, vol. 73.
Shibata, et al., Effects of Vitamin B6 Deficiency on the Conversion Ratio of Tryptophan to Niacin, Biosci. Biotech. Biochem, 1995, pp. 2060-2063, vol. 59, No. 11.
Babu, et al., Hypolipidemic action of curcumin, the active principle of termeric (*Curcuma longa*) in streptozotocin induced diabetic rats, Molecular and Cellular Biochemistry, 1997, pp. 169-175, vol. 166.
Aggarwal, et al., Anticancer Potential of Curcumin: Preclinical and Clinical Studies, 2003, Anticancer Research, pp. 363-698, vol. 23.

(Continued)

*Primary Examiner*—Ruth A Davis
*Assistant Examiner*—Sheridan R MacAuley
(74) *Attorney, Agent, or Firm*—Brian S. Steinberger; Law Offices of Brian Steinberger, P.A.

(57) ABSTRACT

Dietary supplements, compositions and methods of administering the supplements to reduce pain, inflammation and stiffness in said mammal within a few hours. The supplements and compositions can include a combination of an amino acid, vitamins, herbs and enzymes. The composition/supplement can be put in capsule form and when administered to mammals can reduce these symptoms within approximately two hours. reducing the pain and inflammation associated with chronic joint discomfort, chronic low back pain, muscle strain, arthritis, sports injuries, normal everyday bumps and bruises. The novel composition has also been shown to be very effective in reducing monthly menstrual symptoms (PMS). The novel composition can also have benefits for other ailments such as but not limited to Osteoarthritis, Cardiovascular disease, Neurological ailments, Alzheimer disease, and Cancer.

4 Claims, No Drawings

OTHER PUBLICATIONS

Chainani-Wu, Nita, Safety and Anti-Inflammatory Activity of Curcumin: A Component of Tumeric (*Curcuma longa*), The Journal of Alternative and Complementary Medicine, 2003, pp. 161-168, vol. 9, No. 1.

Poeckel, et al., Boswellic Acids: Biological Actions and Molecular Targets, Current Medicinal Chemistry, 2006, pp. 3359-3369, vol. 13.

Kimmatkar, et al., Efficacy and tolerability of *Boswellia serrata* extract in treatement of osteoarthritis of knee—A randomized double blind placebo controlled trial, Phytomedicine, 2003, pp. 3-4, vol. 10.

Wochenschr, Wien Med, Boswelliasauren(Inhaltsstoffe des Weihrauchs) als wirksame Prinzipien zur Behandlung chronisch entzundlicher Erkrankungen, Aus dem Lehrstuhl Pharmakologic fur Naturwissenschaftler, 2002, pp. 373-378, vol. 152, No. 15-16.

Quercetin, University of Maryland Medical Center, Center of integrative medicine, http://www/altmed/ConSupplements/Quercetines.htm, Date: 2008.

Kelly, Gregory S., Bromelain: A Literature Review and Discussion of its Therapeutic Applications, Alternative Medicine Review, 1996, pp. 243-257, vol. 1, No. 4.

Orsini, et al., Bromelain, Plast Reconstr Surg, 2006, pp. 1640-1644, vol. 118, No. 7.

Masse, et al., A Cartilage Matrix Deficiency Experimentally Induced by Vitamin B6 Deficiency, Proc Soc Exp Biol Med., 1998, pp. 97-101, vol. 217, No. 1.

Sanderson, et al., Serum Pyridoxal in patients with rheumatoid arthritis, Ann. rheum. Dis., 1976, pp. 177-180, vol. 35, No. 2.

Ammon, HP, Boswellic Acids in Chronic Inflammatory Diseases, Dept. of Pharmacology, Institute of Pharmaceutical Sciences, University of Tuebingen, Tuebingen, Germany. sekretariat.ammon@uni-tuebingen.de, Date: 2006.

Reichling, et al., Dietary support with Boswellia resin in canine inflammatory joint and spinal disease, 2004, pp. 71-79, vol. 146, No. 2.

Shakibaei, et al., Suppression of NG-kB activation by curcumin leads to inhibition of expression of cyclo-oxygenase-2 and matrix metalloproteinase-9 in human articular chonodrocytes: Implications for the treatment of osteoarthritis, Biochem Pharmacol., 2007, pp. 1434-1445, vol. 73, No. 9.

Akhtar, et al., Oral enzyme combination versus diclofenac in the treatment of osteoarthritis of the knee—a double-blind prospective randomized study, Clin Rheumatol., 2004, pp. 410-415, vol. 23, No. 5.

Walker, et al., Bromelain reduces mild acute knee pain and improves well-being in a dose-dependent fashion in an open study of otherwise healthy adults, Phytomedicine, 2002, pp. 681-686, vol. 9, No. 8.

Sico, Domenic A., Loop Diuretic Therapy, Thiamine Balance, and Heart Failure, pp. 244-247, vol. 13, No. 4, Date: 2007.

Suter, et al., Diuretics and Vitamin B1: Are Diuretics a Risk Factor for Thiamin Malnutrition?, Nutr Rev., 2000, pp. 319-323, vol. 58, No. 10.

Oliveira, et al., Abolition of reperfusion-induced arrhythmias in hearts from thiamine-deficient rats, Am J Physical Heart Circ Physiol, 2007, pp. H394-H401, vol. 293.

Allard, et al., The management of conditioned nutritional requirements in heart failure, Heart Fail Rev, 2006, pp. 75-825, vol. 11.

Lin, et al., Low Pyridoxal 5'-phosphate is associated with increased risk of coronary artery disease, Applied nutritional investigation, 2006, pp. 1146-1151, vol. 22.

Endo, et al., Antioxidant activity of vitamin B6 delays homocysteine-induced atherosclerosis in rats, British Journal of Nutrition, 2006, pp. 1088-1093, vol. 95.

Friso, et al., Low plasma vitamin B-6 concentrations and modulation of coronary artery disease risk 1, 2, 3, Am J Clin Nutr., 2004, pp. 992-998, vol. 79, No. 6.

Harper, Clive, The neurotoxicity of alcohol, Hum Exp Toxicol., 2007, pp. 251-251, vol. 26, No. 3.

Savage, et al., Selective septohippocampal—but not forebrain amygdalar—cholinergic dysfunction in diencephalic amnesia, Brain Res., 2007, pp. 210-219, vol. 1139.

Wang, et al., Thiamine Deficiency Induces Endoplasmic Reticulum Stress in Neurons, Neuroscience, 2007, pp. 1045-1056, vol. 144, No. 3.

Vemuganti, et al., Gene expression changes in thalamus and inferior colliculus associated with inflammation, cellular stress, metabolism and structural damage in thiamine deficiency, Eur J Neurosci., 2006, pp. 1172-1188, vol. 23, No. 5.

Krishna, et al., Effect of pyridoxine deficiency on the structural and functional development of hippocampus, Indian J Physiol Pharmacol, 2004, pp. 304-310, vol. 48, No. 3.

Tang, et al., Vitamin B-6 Deficiency Prolongs the Time Course of Evoked Dopamine Release from Rat Striatum 1,2, J Nutr., 2004, pp. 3350-3354, vol. 134, No. 12.

Hvas, et al., Vitamin B6 Level Is Associated with Symptoms of Depression, Psychother Psychosom., 2004, pp. 340-343, vol. 73, No. 6.

Khajavi, et al., Oral Curcumin Mitigates the Clinical and Neuropathological Phenotype of the Trembler-J Mouse: A Potential Therapy for Inherited Neuropathy, Am J Hum Genet, 2007, pp. 438-453, vol. 81, No. 3.

Xu, et al., Curcumin reverses impaired hippocampal neurogenesis and increases serotonin receptor 1A mRNA and brain-derived neurotrophic factor expression in chronically stressed rats, Brain Res., 2007, pp. 9-18, vol. 1162.

Xu, et al., Antidepressant effects of curcumin in the forced swim test and olfactory bulbectomy models of depression in rats, Pharmacol Biochem Behav., 2005, pp. 200-206, vol. 82, No. 1.

Gibson, et al., Thiamine-Dependent Processes and Treatment Strategies in Neurodegeneration, Antioxid Redox Signal, 2007, pp. 1605-1619, vol. 9, No. 10.

Pepersack, et al., Clinical Relevance of Thiamine Status amongst Hospitalized Elderly Patients, Gerontology, 1999, pp. 96-101, vol. 45, No. 2.

Enokido, Yasushi, Disruption of Amino Acid Metabolism in Astrocyte and Neurological Disorders—Possible Implication of Abnormal Glia-neuron Network in Homocystineuria, Brain Nerve, 2007, pp. 731-737, vol. 59, No. 7.

Spinneker, et al., Vitamin B6 status, deficiency and its consequences—an overview, Nutr Hosp, 2007, pp. 7-24, vol. 22, No. 1.

Boniol, et al., Wernicke encephalopathy complicating lymphoma therapy: case report and literature review, South Med J, 2007, pp. 717-719, vol. 100, No. 7.

Foldi, et al., Transketolase protein TKTL1 overexpression: A potential biomarker and therapeutic target in breast cancer, Oncol. Rep., 2007, pp. 841-845, vol. 17, No. 4.

Lee, et al., Thiamin deficiency: A possible major cause of some tumors?, Oncol, Rep., 2005, pp. 1589-1592, vol. 14.

Ishihara, et al., Low Intake of Vitamin B-6 in Associated with Increased Risk of Colorectal Cancer in Japanese Men, J of Nutr, 2007, pp. 1808-1814, vol. 137.

Bolander, Franklyn F., Vitamins: Not just for enzymes, Curr Opin Investig Drugs, 2006, pp. 912-915, vol. 7, No. 10.

* cited by examiner

__US 7,871,609 B2__

SUPPLEMENTS FOR PAIN MANAGEMENT

This invention claims the benefit of priority to U.S. Provisional Patent Application Ser. No. 60/904,710 filed Mar. 2, 2007.

FIELD OF INVENTION

This invention relates to nutrition and diet, in particular to novel dietary supplements, compositions and methods of administering the supplements to reduce pain, inflammation and stiffness in said mammal within a few hours.

BACKGROUND AND PRIOR ART

Various types of medical compositions have been proposed over the years to treat pain and other discomforts. Many of these compositions require actual prescriptions from medical professionals, such as doctors, and the like, that can be both expensive and time consuming to get. For example, a patient would have to meet with a medical professional to be prescribed the prescription, wait at a pharmacy to purchase the sometime expensive prescription and wait over periods of time until the effects of the prescription occur. Also, many drugs have undesirable side-effects that make them unusable for all patients.

Over the counter(OTC) medications that do not require prescriptions have become popular with the use of aspirin or Tylenol® type meds. However, again these over-the-counter medications are not useable or practical for certain types of patients. For example, aspirin is not use recommended to those patients having ulcers and the like.

In addition, most prescriptions and over the counter medications cannot treat and reduce both pain and inflammation in a single dosage within approximately two hours.

Still furthermore, according to recent pain surveys, almost 50% of the population suffers from some type of chronic or acute pain and that the OTC (over the counter) drugs they tried were only about 34% effective. See for example, ABC News/USA Today Stanford University Medical Center poll Apr. 13-19, 2005.

Thus, the need exists for solutions to the above problems with the prior art.

SUMMARY OF THE INVENTION

A primary objective of the present invention is to provide a single dietary supplement composition of different nutrients and methods of administering the compositions that reduces pain and/or inflammation in mammals, in particular humans.

A secondary objective of the present invention is to provide a single dietary supplement composition of different nutrients and methods of administering the compositions that reduces pain and/or inflammation within less than approximately two hours.

A third objective of the present invention is to provide a single dietary supplement composition of different nutrients and methods of administering the compositions that reduces pain and/or inflammation associated with joint discomfort, muscle strains, stiffness and discomfort, muscle strains, stiffness and discomfort related to bumps and bruises.

A fourth objective of the present invention is to provide a single dietary supplement composition and methods of administering the compositions consisting of an amino acid, vitamins, herbs and enzymes.

A fifth objective of the present invention is to provide supplemental compositions, and methods of reducing pain and/or inflammation within less than approximately two hours by administering capsule type forms of a single dietary supplement composition.

A composition for treating pain and inflammation associated with joint discomfort, muscle strains, stiffness and discomfort, muscle strains, stiffness and discomfort related to bumps and bruises, the composition includes: an amino acid, vitamins, herbs and enzymes.

The vitamins can include Vitamin B1 (thiamine) and Vitamin B6 (pyridoxine).

The herbs include: curcumin (turmeric root extract), and *Boswellia serrate* herb extract. The composition can further include a bioflavonoid quercetin. The amino acid can include D,L-Phenylalanine. The enzyme can include Bromelain.

The novel composition has been found effective in reducing the pain and inflammation associated with chronic joint discomfort, chronic low back pain, muscle strain, arthritis, sports injuries, normal everyday bumps and bruises. It has also been shown to be very effective in reducing monthly menstrual symptoms (PMS).

A method of administering a composition supplement to mammals, can include the steps of: providing a composition consisting of an amino acid, vitamins, herbs and enzymes, in capsule form, such as two capsules, administering the capsule to a mammal, and reducing pain, inflammation and stiffness in said mammal within a few hours.

The composition can be effective within less than approximately two hours.

An embodiment of the dietary supplement can consist of: approximately 25 mg of Vitamin B1 (thiamine Hcl), approximately 25 mg of Vitamin B6 (pyridoxine Hcl), approximately 200 mg of Curcumin (from turmeric root extract), approximately 175 mg of *Boswellia Serrata* herb extract, approximately 75 mg of Quercetin (A bioflavonoid), approximately 75 mg of D,L-Phenylalanine (Amino Acid), and approximately 125 mg of Bromelain, wherein the composition is useful for reducing pain, inflammation and stiffness within a few hour time period.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

A novel dietary supplement can include a preferred composition of approximately eight different nutrients. Each nutrient has been independently studied by scientists and researchers and has demonstrated a capacity to reduce pain and/or inflammation in mammals, in particular humans. There is also scientific evidence that there is a synergistic effect with some of the nutrients when combined that produces greater efficacy.

The oral administration of this dietary supplement is useful as a novel method for treating pain and inflammation associated with joint discomfort, muscle strains, stiffness and discomfort, muscle strains, stiffness and discomfort related to bumps and bruises.

Users of the novel invention composition have claimed relief from other types of medical conditions. For example, users have reported shoulder & neck pain of long duration eliminated; severe premenstrual (PMS) pain reduced or eliminated when taken at start of cycle; fibromyalgia symptoms reduced; osteoarthritis knee pain eliminated and severe headache pain relieved. In each of these instances, (and without any reported side-effects) the invention worked where their OTC (over the counter) or prescription medications did not.

Scientific studies of each of the nutrients in the novel nutrient composition have shown an ability to reduce inflammation and pain. Other studies have demonstrated that when two or three of the ingredients were tested simultaneously there was a synergistic effect resulting in a greater degree of relief. None of the referenced studies have indicated a possible conflict or interaction with prescription medications.

An embodiment of the dietary supplement can include a composition consisting of amino acid, vitamins, herbs and enzymes. The vitamins can include Vitamin B1 (thiamine). The vitamins can further include Vitamin B6 (pyridoxine).

The composition can further include curcumin (turmeric root extract).

The composition can further include *Boswellia serrate* herb extract.

The composition can further include a bioflavonoid quercetin.

The composition can further include D,L-Phenylalanine (an amino acid).

The composition can further include the enzyme Bromelain.

A novel method of administering the dietary supplement composition can include the steps of combining the eight different nutrients in a capsule type form. A prescribed dose can include administering the composition to a mammal, such as a human, taking a capsule(s), and reducing pain, inflammation, stiffness in said mammal within two hours.

A preferred embodiment of an actual supplement composition according to the invention can include The formulation of this supplement can consist of seven components:

1. 25 mg of Vitamin B1 (thiamine (Hcl) hydrochloride);

2. 25 mg of Vitamin B6 (pyridoxine (Hcl) hydrochloride);

3. 200 mg of Curcumin (from turmeric root extract) root dried extract, min. 95% curcuminoids;

4. 175 mg of *Boswellia Serrata* herb extract (serrata gum resin, dried extract, min. 65% boswellic acids);

5. 75 mg of Quercetin (A bioflavonoid) as quercetin dehydrate;

6. 75 mg of D,L-Phenylalanine (DLPA) (Amino Acid); and 7. 125 mg of Bromelain (pineapple).

A description of each of the seven (7) components will now be described.

1. Vitamin B1.

Thiamine is one of the B vitamins, a group of water-soluble vitamins that participate in many of the chemical reactions in the body. Water-soluble vitamins dissolve in water. The body cannot store them. Leftover amounts of the vitamin leave the body through the urine. That means you need a continuous supply of such vitamins in your diet.

Thiamine (vitamin B1) helps the body cells convert carbohydrates into energy. It is also essential for the functioning of the heart, muscles, and nervous system. A 1998 German study demonstrated that high doses of B1, B6, and B12 administered separately or in combination can alleviate acute pain. Therapeutic effects were observed in neuropathic pain and pain of musculoskeletal origin. See for example, Leklem J E. Vitamin B6. In: Shils M E, Olson J A, Shike M, Ross A C, ed. Modern Nutrition in Health and Disease. 9th ed. Baltimore: Williams and Wilkins, 1999: 413-421.

An 1996 Indian scientific study of 556 girls aged 12-21 yr. having moderate to very severe spasmodic dysmenorrhea were given an oral daily dose of 100 mg of Vitamin B1 for 90 days. 87 percent were completely cured, 8 percent relieved (pain almost nil to reduced) and 5 percent showed no effect whatsoever. See Jurna I, Schmerz. 1998 Apr. 20; 12(2): 136-141. Analgesic and analgesia-potentiating action of B vitamins [Article in German].

2. Vitamin B6 is a water-soluble vitamin. It performs a wide variety of functions in your body and is essential for your good health. For example, vitamin B6 is needed for more than 100 enzymes involved in protein metabolism. It is also essential for red blood cell metabolism. The nervous and immune systems need vitamin B6 to function efficiently, and it is also needed for the conversion of tryptophan (an amino acid) to niacin (a vitamin) See Gokhale, L B. Indian J Med Res. 1996 April; 103:22731 Curative treatment of primary (spasmodic) dysmenorrheal; Leklem J E. Vitamin B6. In: Shils M E, Olson J A, Shike M, Ross A C, ed. Modem Nutrition in Health and Disease. 9th ed. Baltimore: Williams and Wilkins, 1999: 413-421; Gerster H. The importance of vitamin B6 for development of the infant. Human medical and animal experiment studies. Z Ernahrungswiss 1996; 35:309-17; Bender D A. Novel functions of vitamin B6. Proc Nutr Soc 1994; 53:625-30; Chandra R and Sudhakaran L. Regulation of immune responses by Vitamin B6. NY Acad Sci 1990; 585:404-423; Trakatellis A, Dimitriadou A, Trakatelli M. Pyridoxine deficiency: New approaches in immunosuppression and chemotherapy. Postgrad Med J 1997; 73:617-22; and Shibata K, Mushiage M, Kondo T, Hayakawa T, Tsuge H. Effects of vitamin B6 deficiency on the conversion ratio of tryptophan to niacin. Biosci Biotechnol Biochem 1995; 59:2060-3.

3. Curcumin.

Inflammation is now recognized as an overwhelming burden to the healthcare status of our population and the underlying basis of a significant number of diseases. Curcumin (a component or turmeric) has long been used as a spice and food-coloring agent. In experimental animals, curcumin has shown anti-diabetic, anti-inflammatory, cytotoxic and antioxidant properties as well as a lipid lowering effect. See Kandarkar S V, Sawani S S, Ingle, A D, et al. Subchronic oral hepatotoxicity of turmeric in mice—histopathological and ultra structural studies. Indian J Exp Biol 1998 July; 36(7): 675-670.

It possesses divers anti-inflammatory and anti-cancer properties following oral or topical administration. Babu P S, et al. Hypolipidemic action of curcumin, the active principle of turmeric (*Curcuma longa*) in streptozocin induced diabetic rats. Mol Cell Biochem. 1997; 166:169-175.

Curcumin was found to be pharmacologically safe in human clinical trials with doses up to 10/grams/day. See for example, Aggarwal B B, Kumar A, Bharti A C. "Anticancer potential of Curcumin: preclinical and clinical studies." Anticancer Res. 2003 January-February; 23(1A):363-98.

A phase 1 human trial with 25 subjects using up to 8000 mg of Curcumin per day for 3 months found no toxicity from Curcumin. Chainani-Wu N. "Safety and anti-inflammatory activity of Curcumin: a component of turmeric (*Curcuma longa*)." J Altern Complement Med. 2003 Feb. 9(1):161-8.

4. BOSWELLIA. Gum resin extracts of *Boswellia* species have been traditionally applied in folk medicine for centuries to treat various chronic inflammatory diseases, and experimental data from animal models and studies with human subjects confirmed the potential of *Boswellia* species extracts for the treatment of not only inflammation but also cancer. See Curr Med Chem. 2006; 13(28):3359-69. Boswellic acids: biological actions and molecular targets.

Osteoarthritis is a common, chronic, progressive, skeletal, degenerative disorder, which commonly affects the knee joint. *Boswellia serrata* extract was demonstrated to be effective in reducing knee pain, decreased swelling in the knee joint, increased knee flexion and increased walking distance. Kimmatkar N, Thawani V, et al. Phytomedicine, 2003 January; 10(1):3-7. Efficacy and tolerability of *Boswellia serrata* extract in treatment of osteoarthritis of knee—a randomized double blind placebo controlled trial.

In clinical trials promising results were observed in patients with rheumatoid arthritis, chronic colitis, ulcerative colitis, Chrohn's disease, bronchial asthma and perituomoral brains edemas. Wien Med Wochenschr. 2002; 152(15-16): 373-8. Boswellic acids (components of frankincense) as the active principle in treatment of chronic inflammatory diseases. [Article in German].

5. QUERCITIN. Quercetin belongs to a group of plant pigments called flavonoids. Flavonoids, such as quercetin provide many health-promoting benefits. Quercetin can act as an antihistamine (help in reducing allergy symptoms) and help reduce inflammation associated with various forms of arthritis. Quercetin also works as an antioxidant by scavenging damaging particles in the body known as free radicals. University of Maryland Medical Center, Center of integrative medicine. http://www/altmed/ConSupplements/Quercetines.htm 6. DLPA Phenylalanine. There are three different types of this amino acid. They are the L form, the D form and the D-L form. They show differing reactions on the body. L-phenylalanine: is associated with nervous states and has anti-depressant properties. D-phenylalanine: enhances the effects of painkillers. It has also been used for Parkinson's Disease and has anti-depressant properties. The memory of some patients may be enhanced with this form of amino acid.

DL-phenylalanine: can be used as a painkiller, especially for chronic, long-term pain e.g., arthritis. It may also be beneficial to people suffering from skin conditions e.g., vitiligo. DLPA works by slowing down the enzymes that degrade the biological Endorphins (neurohormones) produced in the brain. Edorphins are our "natural" internal painkillers and mood elevators. DLPA increases endorphin concentrations and provides additional comfort against chronic aches and pains, as well as helping to relieve depression and premenstrual syndrome (PMS) conditions. See DLPA To End Chronic Pain and Depression by Arnold Fox, M.D. and Barry Fox. Published in 1985 by Long Shadow Books (New York, N.Y.).

7. BROMELAIN. Bromelain is not a single substance, but rather a collection of enzymes and other compounds. It is a mixture of sulfur-containing protein-digesting enzymes— called proteolytic enzymes or proteases. Bromelain can be used in a vast array of medical conditions. It was first introduced in this area in 1957, and works by blocking some proinflammatory metabolites that accelerate and worsen the inflammatory process. It is an anti-inflammatory agent, and so can be used for sports injury, trauma, arthritis, and other kinds of swelling. See Kelly G. S. N. D. Bromelain: A Literature Review and Discussion of it Therapeutic Applications (Alt Med Rev 1996; 1(4):243-257).

Bromelain may be of interest to plastic surgeons because of its apparent ability to reduce pain, edema, inflammation, and platelet aggregation, as well as its ability to potentiate antibiotics. Orsini R. A. Plast Reconstr Surg 2006 December; 118 (7):1640-4. Bromelain.

The novel composition includes components that have been found beneficial for various ailments other than pain and inflammations such as but not limited to Osteoarthritis, Cardiovascular disease, Neurological ailments, Alzheimer disease, and Cancer.

Osteoarthritis—Vitamin B6
Proc Soc Exp Biol Med. 1998 January; 217(1):97-1
A cartilage matrix deficiency experimentally induced by vitamin B6 deficiency. Massé P G, Ziv I, Cole D E, Mahuren J D, Donovan S M, Yamauchi M, Howell D S. Ecole de Nutrition et Etudes Familiales, Université de Moncton, New Brunswick, Canada.

In this article, a vitamin B6-deficiency-induced disorder in avian articular cartilage resembling osteoarthritis has been further characterized. We measured several parameters of proteoglycan (PG) metabolism, i.e., fixed charge density and sulfated glycosaminoglycans (S-GAG) content in PN-deficient versus control articular cartilage and synovial fluid from the knee joint. Statistically significant changes were: 1) decreased content and increased extractability of total sulfated PGs from articular cartilage with guanidine HCl; 2) elevation of S-GAG concentration in synovial fluid; 3) increased plasma cystathionine (sulfur amino acid) levels. PG synthesis as assessed by 35SO4 incorporation into S-GAGs was not impaired. A lack of cartilage swelling in 0.15 M saline and the normal water content indicated that although disturbed, the collagen network was not disrupted. This finding was in agreement with a previous microscopic study that revealed no fissures in the articular cartilage. Previous findings of a normal aggregating PG size-distribution and absence of elevated metalloproteases made a disturbance of aggregating PG metabolism unlikely. Escape into the synovial fluid of small PGs, normally bound to articular collagen, was believed to result from an alteration in collagen molecular organization that could be secondary to elevated circulating SH-compounds.

Ann Rheum Dis. 1976 April; 35(2):177-80.
Serum pyridoxal in patients with rheumatoid arthritis.
Sanderson C R, Davis R E, Bayliss C E.

In this article, abnormalities of tryptophan metabolism have been reported in patients with rheumatoid arthritis (RA) and it has been suggested that these abnormalities are the result of disordered vitamin B6 metabolism. Fasting serum pyridoxal, assayed by an automated microbiological system, was found to be below normal in 35 out of 42 patients with RA while a similar abnormality was found in 8 out of 35 patients with osteoarthritis (OA). Within the RA group the abnormality could not be related to the age, sex, or drug therapy of individuals but of the 8 patients with OA and a low serum pyridoxal, 7 were receiving indomethacin either alone or in conjunction with aspirin.

Osteoarthritis—*Boswellia Serrata*
Ann Rheum Dis. 1976 April; 35(2):177-80.
Planta Med. 2006 October; 72(12):1100-16.
Boswellic acids in chronic inflammatory diseases.
Ammon HP.
Dept. of Pharmacology, Institute of Pharmaceutical Sciences, University of Tuebingen, Tuebingen, Germany. sekretariat.ammon@uni-tuebingen.de In this article Oleogum resins from *BOSWELLIA* species are used in traditional medicine in India and African countries for the treatment of a variety of diseases. Animal experiments showed anti-inflammatory activity of the extract. The mechanism of this action is due to some boswellic acids. It is different from that of NSAID and is related to components of the immune system. The most evident action is the inhibition of 5-lipoxygenase. However, other factors such as cytokines (interleukins and TNF-alpha) and the complement system are also candidates. Moreover, leukocyte elastase and oxygen radicals are targets. Clinical studies, so far with pilot character, suggest efficacy in some autoimmune diseases including rheumatoid arthritis, Crohn's disease, ulcerative colitis and bronchial asthma. Side effects are not severe when compared to modern drugs used for the treatment of these diseases.

Schweiz Arch Tierheilkd. 2004 February; 146(2):71-9

Dietary support with *Boswellia* resin in canine inflammatory joint and spinal disease. Reichling J, Schmökel H, Fitzi J, Bucher S, Saller R. Institut für Pharmazie und Molekulare Biotechnologie (IPMB), Abteilung Biologie, Ruprecht-Karls-University Heidelberg, Germany. Juergen.Reichling@t-online.de In this article, an open multi-centre veterinary clinical trial, comparing conditions before and after treatment with an herbal dietary supplement consisting of a natural resin extract of *Boswellia serrata*, was conducted by 10 practicing veterinarians in Switzerland. This traditional plant-based supplement is known for its anti-rheumatic and anti-inflammatory properties. 29 dogs with manifestations of chronic joint and spinal disease were enrolled. Osteoarthritis and degenerative conditions were confirmed radiologically in 25 of 29 cases. The resin extract (BSB108, product of Bogar AG) was administered with the regular food at a dose of 400 mg/10 kg body weight once daily for 6 weeks. Already after two weeks of treatment, an overall efficacy of the dietary supplement was evident in 71% of 24 eligible dogs. A statistically significant reduction of severity and resolution of typical clinical signs in individual animals, such as intermittent lameness, local pain and stiff gait, were reported after 6 weeks. Effects of external factors that aggravate lameness, such as "lameness when moving" and "lameness after a long rest" diminished gradually. In 5 dogs, reversible brief episodes of diarrhea and flatulence occurred, but only once was a relationship to the study preparation suspected. Because quality and stability of the resin extract were ensured, these data suggest that a standardized preparation can be recommended as an herbal dietary supplement providing symptomatic support in canine osteoarthritis disease.

Phytomedicine. 2003 January; 10(1):3-7.

Efficacy and tolerability of *Boswellia serrata* extract in treatment of osteoarthritis of knee—a randomized double blind placebo controlled trial.

Kimmatkar N, Thawani V, Hingorani L, Khiyani R. MS Orthopedics, Indira Gandhi Medical College, Nagpur, India.

This article describes Osteoarthritis is a common, chronic, progressive, skeletal, degenerative disorder, which commonly affects the knee joint. *Boswellia serrata* tree is commonly found in India. The therapeutic value of its gum (guggulu) has been known. It posses good anti-inflammatory, anti-arthritic and analgesic activity. A randomized double blind placebo controlled crossover study was conducted to assess the efficacy, safety and tolerability of *Boswellia serrata* Extract (BSE) in 30 patients of osteoarthritis of knee, 15 each receiving active drug or placebo for eight weeks. After the first intervention, washout was given and then the groups were crossed over to receive the opposite intervention for eight weeks. All patients receiving drug treatment reported decrease in knee pain, increased knee flexion and increased walking distance. The frequency of swelling in the knee joint was decreased. Radiologically there was no change. The observed differences between drug treated and placebo being statistically significant, are clinically relevant. BSE was well tolerated by the subjects except for minor gastrointestinal ADRs. BSE is recommended in the patients of osteoarthritis of the knee with possible therapeutic use in other arthritis.

Osteoarthritis—Curcumin

Biochem Pharmacol. 2007 May 1; 73(9):1434-45. Epub 2007 Jan. 7. Suppression of NF-kappaB activation by curcumin leads to inhibition of expression of cyclo-oxygenase-2 and matrix metalloproteinase-9 in human articular chondrocytes: Implications for the treatment of osteoarthritis. Shakibaei M, John T, Schulze-Tanzil G, Lehmann I, Mobasheri A. Institute of Anatomy, Ludwig-Maximilians-University Munich, Pettenkoferstrasse 11, D-80336 Munich, Germany. mehdi.shakibaei@med.uni-muenchen.de This article discusses pro-inflammatory cytokines such as interleukin-1beta (IL-1beta) and tumor necrosis factor-alpha (TNF-alpha) play a key role in the pathogenesis of osteoarthritis (OA). Anti-inflammatory agents capable of suppressing the production and catabolic actions of these cytokines may have therapeutic potential in the treatment of OA and a range of other osteoarticular disorders. The purpose of this study was to examine the effects of curcumin (diferuloylmethane), a pharmacologically safe phytochemical agent with potent anti-inflammatory properties on IL-1 beta and TNF-alpha signalling pathways in human articular chondrocytes maintained in vitro. The effects of curcumin were studied in cultures of human articular chondrocytes treated with IL-1 beta and TNF-alpha for up to 72 h. Expression of collagen type II, integrin beta II, cyclo-oxygenase-2 (COX-2) and matrix metalloproteinase-9 (MMP-9) was monitored by western blotting.

The effects of curcumin on the expression, phosphorylation and nuclear translocation of protein components of the NF-kappaB system were studied by western blotting and immunofluorescence, respectively. Treatment of chondrocytes with curcumin suppressed IL-1beta-induced NF-kappaB activation via inhibition of IkappaBalpha phosphorylation, IkappaBalpha degradation, p65 phosphorylation and p65 nuclear translocation. Curcumin inhibited the IL-1beta-induced stimulation of up-stream protein kinase B Akt. These events correlated with down-regulation of NF-kappaB targets including COX-2 and MMP-9. Similar results were obtained in chondrocytes stimulated with TNF-alpha. Curcumin also reversed the IL-1beta-induced down-regulation of collagen type II and beta1-integrin receptor expression. These results indicate that curcumin has nutritional potential as a naturally occurring anti-inflammatory agent for treating OA through suppression of NF-kappaB mediated IL-1beta/TNF-alpha catabolic signalling pathways in chondrocytes.

Osteoarthritis—Bromelain

Clin Rheumatol. 2004 October; 23(5):410-5. Epub 2004 Jul. 24. Oral enzyme combination versus diclofenac in the treatment of osteoarthritis of the knee—a double-blind prospective randomized study. Akhtar N M, Naseer R, Farooqi A Z, Aziz W, Nazir M. Pakistan King Edward Medical College Lahore, Mayo Hospital.

The aim of this study was to compare the efficacy and safety of an oral enzyme-rutosid combination (ERC) containing rutosid and the enzymes bromelain and trypsin, with that of diclofenac in patients with osteoarthritis (OA) of the knee.

A total of 103 patients presenting with painful episodes of OA of the knee were treated for 6 weeks in two study centers in a randomized, double-blind, parallel group trial. Altogether, 52 patients were treated in the ERC group and 51 patients were treated in the diclofenac group. Primary efficacy criteria were Lequesne's Algofunctional Index (LFI) and a 'complaint index', including pain at rest, pain on motion and restricted function. The efficacy criteria were analyzed by applying the Wilcoxon-Mann-Whitney test that provides the Mann-Whitney estimator (MW) as a measure of relevance. Non-inferiority was considered to be proven if the lower bound of the 97.5% one-sided confidence interval (CI-LB) was higher than MW=0.36 (benchmark of not yet relevant inferiority).

Both treatments resulted in clear improvements. Within the 6-week observation period, the mean value of the LFI decreased from 13.0 to 9.4 in the ERC group and from 12.5 to 9.4 in the diclofenac group. Non-inferiority of ERC was demonstrated by both primary criteria, LFI (MW=0.5305; CI-LB=0.4171) and complaint index (MW=0.5434; CI-LB=0.4296). Considerable improvements were also seen in secondary efficacy criteria, with a slight tendency towards superiority of ERC. The global judgment of efficacy by physician resulted in at least good ratings for 51.4% of the ERC patients, and for 37.2% of the diclofenac patients. In the majority of patients tolerability was judged in both drug groups as very good or good. The current study indicates that ERC can be considered as an effective and safe alternative to NSAIDs such as diclofenac in the treatment of painful episodes of OA of the knee. Placebo-controlled studies are now needed to confirm these results.

Phytomedicine. 2002 December; 9(8):681-6.

Bromelain reduces mild acute knee pain and improves well-being in a dose-dependent fashion in an open study of otherwise healthy adults. Walker A F, Bundy R, Hicks S M, Middleton R W. Hugh Sinclair Unit of Human Nutrition, The University of Reading, UK. a.f.walker@reading.ac.uk This article describes preliminary clinical evidence to support the contention that the anti-inflammatory and analgesic properties of bromelain help to reduce symptoms of osteo- and rheumatoid arthritis. However, there have been no controlled studies of its effects on joint health in healthy subjects who lack such diagnosis. The current study investigated the effects of bromelain on mild acute knee pain of less than 3 months duration in otherwise healthy adults. The study was an open, dose-ranging postal study in volunteers who had been recruited through newspaper and magazine articles. Two validated questionnaires (WOMAC knee health Index and the Psychological Well-Being Index) were completed at baseline and after one month's intervention with bromelain, randomly allocated to volunteers as either 200 mg or 400 mg per day. Seventy seven subjects completed the study. In both treatment groups, all WOMAC symptom dimension scores were significantly reduced compared with baseline, with reductions in the final battery (total symptom score) of 41 and 59% (P=0.0001 and <0.0001) in the low and high dose groups respectively. In addition, improvements in total symptom score (P=0.036) and the stiffness (P=0.026) and physical function (P=0.021) dimensions were significantly greater in the high-dose (400 mg per day) compared with the low-dose group. Compared to baseline, overall psychological well-being was significantly improved in both groups after treatment (P=0.015 and P=0.0003 in the low and high dose groups respectively), and again, a significant dose-response relationship was observed. We conclude that bromelain may be effective in ameliorating physical symptoms and improving general well-being in otherwise healthy adults suffering from mild knee pain in a dose-dependant manner. Double blind, placebo-controlled studies are now warranted Cardiovascular—Thiamine Congest Heart Fail. 2007 July-August; 13(4):244-7 Loop diuretic therapy, thiamine balance, and heart failure. Sica D A. Section of Clinical Pharmacology and Hypertension, Division of Nephrology, Medical College of Virginia of Virginia Commonwealth University, Richmond, Va. 23298-0160, USA. dsica@mcvh-vcu.edu This article describes Thiamine, or vitamin B1, is a water-soluble B complex vitamin that was first discovered in 1910 in the process of exploring how rice bran cured patients of beriberi. Thiamine is not synthesized in humans, therefore its availability for necessary cellular processes hinges on its continual ingestion. The amount of thiamine one needs to ingest to maintain balance is disease state-dependent or medication-dependent. Severe chronic thiamine deficiency can have significant neurologic and cardiac effects, the latter is reflected in a particular type of heart failure called wet beriberi. This form of heart failure clearly benefits from thiamine supplementation. It is unclear, however, whether thiamine supplementation offers any benefit in other forms of heart failure. Despite this, it is not unreasonable for heart failure patients to routinely ingest a thiamine-containing multivitamin; patients using diuretics have an increased urinary excretion of thiamine and thus are at a higher risk for developing thiamine deficiency. The role of thiamine in heart failure, however, remains arguable.

Nutr Rev. 2000 October; 58(10):319-23, Diuretics and vitamin B1: are diuretics a risk factor for thiamin malnutrition? Suter P M, Vetter W. Medical Policlinic, University Hospital, Zurich, Switzerland.

This article describes that despite modern pharmacologic agents in the therapy of heart failure, the prevalence of heart failure is increasing worldwide. In the vitamin B1 deficiency disease beriberi, cardiac symptoms may represent the central feature. Two new studies confirmed that all diuretics lead to increased urinary thiamin excretion depending on the urinary flow rate. In a subject at risk, such as an elderly patient, chronic diuretic treatment may lead to a subclinical thiamin deficiency. Whether subclinical thiamin nutriture is a modulator of the prevalence and/or severity of heart failure is not known; however, it seems to be plausible from the metabolic point of view.

Am J Physiol Heart Circ Physiol. 2007 July; 293(1):H394-401. Epub 2007 Mar. 16. Abolition of reperfusion-induced arrhythmias in hearts from thiamine-deficient rats. Oliveira F A, Guatimosim S, Castro C H, Galan D T, Lauton-Santos S, Ribeiro A M, Almeida A P, Cruz J S. Department of Biochemistry and Immunology, Biological Sciences Institute, Universidade Federal de Minas Gerais, Belo Horizonte, MG, CEP 31900-901, Brazil.

This article describes extensive work has been done regarding the impact of thiamine deprivation on the nervous system. In cardiac tissue, chronic thiamine deficiency is described to cause changes in the myocardium that can be associated with arrhythmias. However, compared with the brain, very little is known about the effects of thiamine deficiency on the heart. Thus this study was undertaken to explore whether thiamine deprivation has a role in cardiac arrhythmogenesis. We examined hearts isolated from thiamine-deprived and control rats. We measured heart rate, diastolic and systolic tension, and contraction and relaxation rates. Whole cell voltage clamp was performed in rat isolated cardiac myocytes to measure L-type $Ca(2+)$ current. In addition, we investigated the global intracellular calcium transients by using confocal microscopy in the line-scan mode. The hearts from thiamine-deficient rats did not degenerate into ventricular fibrillation during 30 min of reperfusion after 15 min of coronary occlusion. The anti-arrhythmogenic effects were characterized by the arrhythmia severity index. Our results suggest that hearts from thiamine-deficient rats did not experience irreversible arrhythmias. There was no change in L-type Ca(2+) current density. Inactivation kinetics of this current in Ca(2+)-buffered cells was retarded in thiamine-deficient cardiac myocytes. The global Ca(2+) release was significantly reduced in thiamine-deficient cardiac myocytes. The amplitude of caffeine-releasable Ca(2+) was lower in thiamine-deficient myocytes. In summary, we have found that thiamine deprivation attenuates the incidence and severity of postischemic arrhythmias, possibly through a mechanism involving a decrease in global Ca(2+) release.

Heart Fail Rev. 2006 March; 11(1):75-82.

The management of conditioned nutritional requirements in heart failure, Allard M L, Jeejeebhoy K N, Sole M J., Division of Cardiology, University Health Network, Toronto, Ontario.

This article describes patients suffering from congestive heart failure exhibit impaired myocardial energy production, myocyte calcium overload and increased oxidative stress. Nutritional factors known to be important for myocardial energy production, calcium homeostasis and the reduction of oxidative stress, such as thiamine, riboflavin, pyridoxine, L-carnitine, coenzyme Q10, creatine and taurine are reduced in this patient population. Furthermore, deficiencies of taurine, carnitine, and thiamine are established primary causes of dilated cardiomyopathy. Studies in animals and limited trials in humans have shown that dietary replacement of some of these compounds in heart failure can significantly restore depleted levels and may result in improvement in myocardial structure and function as well as exercise capacity. Larger scale studies examining micronutrient depletion in heart failure patients, and the benefits of dietary replacement need to be performed. At the present time, it is our belief that these conditioned nutritional requirements, if unsatisfied, contribute to myocyte dysfunction and loss; thus, restoration of nutritional deficiencies should be part of the overall therapeutic strategy for patients with congestive heart failure.

Cardiovascular—Vitamin B6

Nutrition. 2006 November-December; 22(11-12):1146-51. Epub 2006 Oct. 10. Low pyridoxal 5'-phosphate is associated with increased risk of coronary artery disease. Lin P T, Cheng C H, Liaw Y P, Lee B J, Lee T W, Huang Y C. School of Nutrition, Chung Shan Medical University, Taichung, Taiwan.

The purpose of this study was to investigate the association between plasma pyridoxal 5'-phosphate (PLP) status and lipid profiles and to estimate the relation to the risk of coronary artery disease (CAD). METHODS: Patients who were identified by cardiac catheterization as having > or =70% stenosis of one major coronary artery were assigned to the case group (n=184). The control group (n=516) was comprised of healthy individuals with normal blood biochemical values. Plasma PLP, homocysteine, high-sensitivity C-reactive protein, lipid profiles (total cholesterol, low-density lipoprotein, high-density lipoprotein, very low-density lipoprotein, and triacylglycerol) were determined. RESULTS: Subjects with a plasma PLP level <30 nmol/L exhibited a significantly increased risk of CAD compared with subjects with a plasma PLP level > or =30 nmol/L (odds ratio, 1.85; 95% confidence interval, 1.16-2.95) after adjusting for homocysteine and high-sensitivity C-reactive protein. The association between PLP and the risk of CAD remained significant after each lipid profile was additionally adjusted. In addition, the combined presence of low PLP level and an abnormal lipid level increased the risk of CAD to an even greater degree. CONCLUSIONS: A borderline vitamin B6 deficiency (plasma PLP concentration <30 nmol/L) is strongly associated with the risk of CAD. The combined presence of low PLP and abnormal lipid levels increased the risk of CAD even further.

Br J Nutr. 2006 June; 95(6):1088-93. Antioxidant activity of vitamin B6 delays homocysteine-induced atherosclerosis in rats. Endo N, Nishiyama K, Otsuka A, Kanouchi H, Taga M, Oka T. Department of Veterinary Physiology, Faculty of Agriculture, Kagoshima University, 1-21-24 Korimoto, Kagoshima 890-0065, Japan.

This article discusses elevated plasma homocysteine is a risk factor for atherosclerotic disease. In the present study, we have examined whether the oxidative stress due to a low level of vitamin B6 accelerates the development of homocysteine-induced atherosclerosis in rats. First, the effect of homocysteine thiolactone intake (50 mg/kg per d) on vascular integrity, lipid peroxide concentration, endothelial NO synthase (eNOS) expression and biochemical profiles was examined at day 1, day 21 and day 42 (five rats per group). The histochemical staining of the rat aorta showed no change at day 1 and day 21, but the subendothelial space was observed to be enlarged in rat aorta at day 42 with exposure to homocysteine thiolactone. Expression of eNOS was observed in rat aorta at day 42, but not at day 1 and day 21. Serum lipid peroxide concentration and biochemical profiles including glucose cholesterol and triacylglycerol showed no change at any day. Second, the effect of homocysteine thiolactone intake in the presence and absence of vitamin B6 on vascular integrity was examined at day 1 and day 14 (five rats per group). Aortic lesions were observed in vitamin B6-deficient rat aorta at day 14 but not in vitamin B6-supplemented rats. The expression of eNOS was also observed in vitamin B6-deficient rat aorta at day 14. Serum lipid concentrations of the vitamin B6-deficient group significantly increased compared with concentrations of the vitamin B6-supplemented group, though serum concentration of homocysteine did not change between both groups. These results suggest that the oxidative stress caused by a low level of vitamin.

Am J Clin Nutr. 2004 June; 79(6):992-8. Low plasma vitamin B-6 concentrations and modulation of coronary artery disease risk. Friso S, Girelli D, Martinelli N, Olivieri O, Lotto V, Bozzini C, Pizzolo F, Faccini G, Beltrame F, Corrocher R. Department of Clinical and Experimental Medicine, University of Verona School of Medicine, Verona, Italy. simonetta.friso@univr.it.

This article describes low concentrations of pyridoxal-5'-phosphate (PLP), the active metabolite of vitamin B-6, are associated with high C-reactive protein (CRP) concentrations. Both low PLP and elevated inflammatory markers, such as high-sensitivity CRP (hs-CRP) and fibrinogen, are related to higher risk of coronary artery disease (CAD). OBJECTIVES: The objectives were to evaluate the relation between PLP and acute-phase reactants in affecting CAD risk and to estimate the risk of CAD related to low plasma PLP, either alone or in combination with high concentrations of acute-phase reactants and other classic risk factors for CAD. DESIGN: A case-control study was conducted with 742 participants: 475 with severe multivessel CAD and 267 free from coronary atherosclerosis (CAD-free). We measured plasma PLP, fibrinogen, hs-CRP, and serum lipid concentrations and all major biochemical CAD risk factors, including total homocysteine. RESULTS: A significant, inverse, graded relation was observed between PLP and both hs-CRP and fibrinogen (P<0.001). The prevalence of PLP concentrations in the lower half of the population (<50th percentile: 36.3 nmol/L) was significantly higher among CAD patients than among CAD-free subjects (P<0.001). The odds ratio for CAD risk related to low PLP concentrations after adjustments for the major classic CAD risk factors, including hs-CRP and fibrinogen, was 1.89 (95% CI:1.18, 3.03; P=0.008). The CAD risk as a result of low PLP was additive when considered in combination with elevated hs-CRP concentrations or with an increased ratio of LDL to HDL. CONCLUSION: Low plasma PLP concentrations are inversely related to major markers of inflammation and independently associated with increased CAD risk.

Neurological—Thiamine

Hum Exp Toxicol. 2007 March; 26(3):251-7. The Neurotoxicity of Alcohol Harper C. Department of Pathology, Blackburn Building, D06, University of Sydney, NSW 2006, Australia. cliveh@med.usyd.edu.au.

This article discusses patterns of drinking are changing throughout the world and in many countries this will be detrimental to the health and welfare of the local population. Even uncomplicated alcoholics who have no specific neurological or hepatic problems show signs of regional brain damage and cognitive dysfunction. Many of these changes are exaggerated and other brain regions damaged in patients who have additional vitamin B1 (thiamine) deficiency (Wernicke-Korsakoff syndrome). Quantitative neuropathology techniques and improvements in neuroimaging have contributed significantly to the documentation of these changes but mechanisms underlying the damage are not understood. A human brain bank targeting alcohol cases has been established in Sydney, Australia and provides fresh and frozen tissue for alcohol researchers. The tissues can be used to test hypotheses developed from structural neuropathological studies or from animal models and in vitro studies. Identification of reversible pathological changes and preventative medical approaches in alcoholism should enhance rehabilitation and treatment efforts, thereby mitigating debilitating morbidities and reducing mortality associated with this universal public health problem.

Brain Res. 2007 Mar. 30; 1139:210-9. Epub 2007 Jan. 8. Selective septohippocampal—but not forebrain amygdalar—cholinergic dysfunction in diencephalic amnesia. Savage L M, Roland J, Klintsova A. Behavioral Neuroscience Program, Department of Psychology, Binghamton University, State University of New York, Binghamton, N.Y. 13902, USA. 1savage@binghamton.edu In this article a rodent model of diencephalic amnesia, pyrithiamine-induced thiamine deficiency (PTD), was used to investigate diencephalic-limbic interactions. In-vivo acetylcholine (ACh) efflux, a marker of memory-related activation, was measured in the hippocampus and the amygdala of PTD-treated and pair-fed (PF) control rats while they were tested on a spontaneous alternation task. During behavioral testing, all animals displayed increases in ACh efflux in both the hippocampus and amygdala. However, during spontaneous alternation testing ACh efflux in the hippocampus and the alternation scores were higher in PF rats relative to PTD-treated rats. In contrast, ACh efflux in the amygdala was not suppressed in PTD treated rats, relative to PF rats, prior to or during behavioral testing. In addition, unbiased stereological estimates of the number of choline acetyltransferase (ChAT) immunopositive neurons in the medial septal/diagonal band (MS/DB) and nucleus basalis of Meynert (NBM) also reveal a selective cholinergic dysfunction: In PTD-treated rats a significant loss of ChAT-immunopositive cells was found only in the MS/DB, but not in the NBM. Significantly, these results demonstrate that thiamine deficiency causes selective cholinergic dysfunction in the septo-hippocampal pathway.

Neuroscience. 2007 Feb. 9; 144(3):1045-56. Epub 2006 Nov. 28, Thiamine deficiency induces endoplasmic reticulum stress in neurons. Wang X, Wang B, Fan Z, Shi X, Ke Z J, Luo J. Institute for Nutritional Sciences, Shanghai Institutes for Biological Sciences, Chinese Academy of Sciences, Shanghai 200031, PR China.

This article discusses that Thiamine (vitamin B1) deficiency (TD) causes region selective neuronal loss in the brain; it has been used to model neurodegeneration that accompanies mild impairment of oxidative metabolism. The mechanisms for TD-induced neurodegeneration remain incompletely elucidated. Inhibition of protein glycosylation, perturbation of calcium homeostasis and reduction of disulfide bonds provoke the accumulation of unfolded proteins in the endoplasmic reticulum (ER), and cause ER stress. Recently, ER stress has been implicated in a number of neurodegenerative models. We demonstrated here that TD up-regulated several markers of ER stress, such as glucose-regulated protein (GRP) 78, growth arrest and DNA-damage inducible protein or C/EBP-homologus protein (GADD153/Chop), phosphorylation of eIF2alpha and cleavage of caspase-12 in the cerebellum and the thalamus of mice. Furthermore, ultrastructural analysis by electron microscopic study revealed an abnormality in ER structure. To establish an in vitro model of TD in neurons, we treated cultured cerebellar granule neurons (CGNs) with amprolium, a potent inhibitor of thiamine transport. Exposure to amprolium caused apoptosis and the generation of reactive oxygen species in CGNs. Similar to the observation in vivo, TD up-regulated markers for ER stress. Treatment of a selective inhibitor of caspase-12 significantly alleviated amprolium-induced death of CGNs. Thus, ER stress may play a role in TD-induced brain damage.

Eur J Neurosci. 2006 March; 23(5):1172-88. Gene expression changes in thalamus and inferior colliculus associated with inflammation, cellular stress, metabolism and structural damage in thiamine deficiency. Vemuganti R, Kalluri H, Yi J H, Bowen K K, Hazell A S. Department of Neurological Surgery, University of Wisconsin, Madison, USA.

This article discusses the identification of gene expression changes that promote focal neuronal death and neurological dysfunction can further our understanding of the pathophysiology of these disease states and could lead to new pharmacological and molecular therapies. Impairment of oxidative metabolism is a pathogenetic mechanism underlying neuronal death in many chronic neurodegenerative diseases as well as in Wernicke's encephalopathy (WE), a disorder induced by thiamine deficiency (TD). To identify functional pathways that lead to neuronal damage in this disorder, we have examined gene expression changes in the vulnerable thalamus and inferior colliculus of TD rats using Affymetrix Rat Genome GeneChip analysis in combination with gene ontology and functional categorization assessment utilizing the NetAffx GO Mining Tool. Of the 15 927 transcripts analysed, 125 in thalamus and 141 in inferior colliculus were more abundantly expressed in TD rats compared with control animals. In both regions, the major functional categories of transcripts that were increased in abundance after TD were those associated with inflammation (approximately 33%), stress (approximately 20%), cell death and repair (approximately 26%), and metabolic perturbation (approximately 19%), together constituting approximately 98% of all transcripts up-regulated. These changes occurred against a background of neuronal cell loss and reactive astro- and microgliosis in both structures. Our results indicate that (i) TD produces changes in gene expression that are consistent with the observed dysfunction and pathology, and (ii) similar alterations in expression occur in thalamus and inferior colliculus, brain regions previously considered to differ in pathology. These findings provide important new insight into processes responsible for lesion development in TD, and possibly WE.

Neurological—Vitamin B6

Indian J Physiol Pharmacol. 2004 July; 48(3):304-1. Effect of pyridoxine deficiency on the structural and functional development of hippocampus. Krishna A P, Ramakrishna T. Department of Physiology, K. S. Hegde Medical Academy, Nithyananda Nagar, Deralakatte, Mangalore-575 018.

In this study it was attempted to understand the effect of pyridoxine deficiency on the structural and functional development of the hippocampus. Hippocampus has been closely associated with complex neuroendocrine control of physiological activities as well as behavioural responses including learning process and memory retention. Prenatal, preweanling and weanling deficiency of pyridoxine was induced in the experimental rats by feeding dams with diet deficient in pyridoxine during pregnancy and lactation. The general growth profile for pyridoxine deficient (PD) rats is compared with control ones. The structural changes in the hippocampus of pyridoxine deficient rats was investigated using the histological techniques. Hippocampal electrical activity was recorded from in vitro brain slice preparation. The study clearly showed the structural impairment in the hippocampus of PD rats. These anatomic anomalies might be related to poor neurointegrative development and neurophysiological deficits that occur in young one. The electrical activity recorded from hippocampal slices of PD rats showed significant variation when compared to controls. Pyridoxine deficiency is common in pregnant women who used anovulatory steroids before pregnancy. The pyridoxine deficiency of the mother may result in permanent behavioural abnormality and intellectual deficit in the progeny.

J Nutr. 2004 December; 134(12):3350-4. Vitamin B-6 deficiency prolongs the time course of evoked dopamine release from rat striatum. Tang F I, Wei I L.

School of Nursing, National Yang-Ming University, Taipei 112, Taiwan.

This article discusses Vitamin B-6-deficient animals exhibit motor abnormalities. To investigate the possible physiologic alterations in the dopaminergic nervous system in vitamin B-6 deficiency, dopamine release in the striatum of vitamin B-6-deficient rats was determined using in vivo electrochemistry. Male Sprague-Dawley rats, 3 wk old, weighing 50-60 g, were randomly assigned to a control (7 mg pyridoxine HCl/kg diet), vitamin B-6-deficient (0 mg pyridoxine HCl/kg diet), or pair-fed (7 mg pyridoxine HCl/kg diet) group. After 8 wk of dietary treatment, plasma concentrations of pyridoxal 5'-phosphate as well as the striatal pyridoxal 5'-phosphate and pyridoxamine 5'-phosphate were significantly lower in the vitamin B-6-deficient group than in the control and pair-fed groups. The dopamine concentrations of the striatum and the magnitude of the dopamine release after local application of KCl did not differ among the groups. However, the time required for KCl-evoked dopamine release to reach its peak level was significantly longer for the vitamin B-6-deficient rats than for controls. In addition, the decay time from the peak to one-half of the KCl-evoked dopamine release was also significantly prolonged in vitamin B-6-deficient rats compared with the control group. The results indicate that the cellular content of dopamine does not reflect the functional state of dopaminergic neurons in vitamin B-6 deficiency. The time course for release of dopamine and decay of the released dopamine is prolonged by vitamin B-6 deficiency, which might contribute to the motor abnormalities of the deficient rats.

Psychother Psychosom. 2004 November-December; 73(6): 340-3. Vitamin B6 level is associated with symptoms of depression. Hvas A M, Juul S, Bech P, Nexø E. Department of Clinical Biochemistry, Aarhus University Hospital, AKH, Aarhus, Denmark. am.hvas@dadlnet.dk This article discusses a low level of vitamin B6 might theoretically cause depression as vitamin B6 is a cofactor in the tryptophan-serotonin pathway. In the present study, we examined the association between depression and the phosphate derivative of vitamin B6 in plasma, pyridoxal phosphate (PLP). METHODS: In 140 individuals, symptoms of depression were evaluated by the Major Depression Inventory, and biochemical markers of vitamin B deficiency were measured. RESULTS: We found that 18 (13%) individuals were depressed. A low plasma level of PLP was significantly associated with the depression score ($p=0.002$). No significant association was found between depression and plasma vitamin B12 ($p=0.13$), plasma methylmalonic acid ($p=0.67$), erythrocyte folate ($p=0.77$), and plasma total homocysteine ($p=0.16$). CONCLUSION: Our study suggests that a low level of plasma PLP is associated with symptoms of depression. Randomized trials are now justified and needed in order to examine whether treatment with vitamin B6 may improve symptoms of depression.

Neurological—Curcumin

Am J Hum Genet. 2007 September; 81(3):438-53. Epub 2007 Aug. 3. Oral curcumin mitigates the clinical and neuropathologic phenotype of the trembler-j mouse: a potential therapy for inherited neuropathy. Khajavi M, Shiga K, Wiszniewski W, He F, Shaw C A, Yan J, Wensel T G, Snipes G J, Lupski J R. From the Department of Molecular and Human Genetics, Baylor College of Medicine, Houston, Tex., 77030, USA.

This article discusses mutations in myelin genes cause inherited peripheral neuropathies that range in severity from adult-onset Charcot-Marie-Tooth disease type 1 to childhood-onset Dejerine-Sottas neuropathy and congenital hypomyelinating neuropathy. Many myelin gene mutants that cause severe disease, such as those in the myelin protein zero gene (MPZ) and the peripheral myelin protein 22 gene (PMP22), appear to make aberrant proteins that accumulate primarily within the endoplasmic reticulum (ER), resulting in Schwann cell death by apoptosis and, subsequently, peripheral neuropathy. We previously showed that curcumin supplementation could abrogate ER retention and aggregation-induced apoptosis associated with neuropathy-causing MPZ mutants. We now show reduced apoptosis after curcumin treatment of cells in tissue culture that express PMP22 mutants. Furthermore, we demonstrate that oral administration of curcumin partially mitigates the severe neuropathy phenotype of the Trembler-J mouse model in a dose-dependent manner. Administration of curcumin significantly decreases the percentage of apoptotic Schwann cells and results in increased number and size of myelinated axons in sciatic nerves, leading to improved motor performance. Our findings indicate that curcumin treatment is sufficient to relieve the toxic effect of mutant aggregation-induced apoptosis and improves the neuropathologic phenotype in an animal model of human neuropathy, suggesting a potential therapeutic role in selected forms of inherited peripheral neuropathies.

Brain Res. 2007 Aug. 8; 1162:9-18. Epub 2007 Jun. 21. Curcumin reverses impaired hippocampal neurogenesis and increases serotonin receptor 1A mRNA and brain-derived neurotrophic factor expression in chronically stressed rats. Xu Y, Ku B, Cui L, Li X, Barish P A, Foster T C, Ogle W O. Department of Biomedical Engineering, University of Florida, Gainesville, Fla., 32611, USA.

This article discusses *Curcuma longa* is a major constituent of Xiaoyao-san, the traditional Chinese medicine, which has been used to effectively manage stress and depression-related disorders in China. As the active component of *curcuma longa*, curcumin possesses many therapeutic properties; we have previously described its antidepressant activity in our earlier studies using the chronic unpredictable stress model of depression in rats. Recent studies show that stress-induced damage to hippocampal neurons may contribute to the pathophysiology of depression. The aim of this study was to investigate the effects of curcumin on hippocampal neurogenesis in chronically stressed rats. We used an unpredictable chronic stress paradigm (20 days) to determine whether chronic curcumin treatment with the effective doses for behavioral responses (5, 10 and 20 mg/kg, p.o.), could alleviate or reverse the effects of stress on adult hippocampal neurogenesis. Our results suggested that curcumin administration (10 and 20 mg/kg, p.o.) increased hippocampal neurogenesis in chronically stressed rats, similar to classic antidepressant imipramine treatment (10 mg/kg, i.p.). Our results further demonstrated that these new cells mature and become neurons, as determined by triple labeling for BrdU and neuronal- or glial-specific markers. In addition, curcumin significantly prevented the stress-induced decrease in 5-HT(1A) mRNA and BDNF protein levels in the hippocampal subfields, two molecules involved in hippocampal neurogenesis. These results raise the possibility that increased cell proliferation and neuronal populations may be a mechanism by which curcumin treatment overcomes the stress-induced behavioral abnormalities and hippocampal neuronal damage. Moreover, curcumin treatment, via up-regulation of 5-HT(1A) receptors and BDNF, may reverse or protect hippocampal neurons from further damage in response to chronic stress, which may underlie the therapeutic actions of curcumin.

Pharmacol Biochem Behav. 2005 September; 82(1):200-6. Antidepressant effects of curcumin in the forced swim test and olfactory bulbectomy models of depression in rats. Xu Y, Ku B S, Yao H Y, Lin Y H, Ma X, Zhang Y H, Li X J. Department of Pharmacology, School of Basic Medical Science, Peking University, China.

This article discusses *Curcuma longa* is a major constituent of Xiaoyao-san, the traditional Chinese medicinal formula, which has been used to effectively manage stress and depression-related disorders in China. Curcumin is the active component of *curcuma longa*, and we hypothesized that curcumin would have an influence on depressive-like behaviors. The purpose of the present study was to confirm the putative antidepressant effect of chronic administrations of curcumin (1.25, 2.5, 5 and 10 mg/kg, p.o.) in the forced swimming test and bilateral olfactory bulbectomy (OB) models of depression in rats. In the first study, chronic treatment with curcumin (14 days) reduced the immobility time in the forced swimming test. In the second experiment, curcumin reversed the OB-induced behavioral abnormalities such as hyperactivity in the open field, as well as deficits in step-down passive avoidance. In addition, OB-induced low levels of serotonin (5-HT), noradrenaline (NA), high 5-hydroxyindoleacetic acid (5-HIAA) and 4-dihydroxyphenylacetic acid (DOPAC) in the hippocampus were observed, and were completely reversed by curcumin administration. A slight decrease in 5-HT, NA and dopamine (DA) levels was found in the frontal cortex of OB rats which was also reversed by curcumin treatment. These results confirm the antidepressant effects of curcumin in the forced swim and the OB models of depression in rats, and suggest that these antidepressant effects may be mediated by actions in the central monoaminergic neurotransmitter systems.

Alzheimer's Disease—Thiamine

Antioxid Redox Signal. 2007 Aug. 8; [Epub ahead of print]. Thiamine-Dependent Processes and Treatment Strategies in Neurodegeneration. Gibson G E, Blass J P. Department of Neurology and Neurosciences, Weill Medical College of Cornell University, Burke Medical Research Institute, White Plains, N.Y.

This article discusses reductions in brain glucose metabolism and increased oxidative stress invariably occur in Alzheimer's disease (AD) and thiamine (vitamin B1) deficiency. Both conditions cause irreversible cognitive impairment; their behavioral consequences overlap but are not identical. Thiamine-dependent processes are critical in glucose metabolism, and recent studies implicate thiamine in oxidative stress, protein processing, peroxisomal function, and gene expression. The activities of thiamine-dependent enzymes are characteristically diminished in AD, and the reductions in autopsy AD brain correlate highly with the extent of dementia in the preagonal state. Abnormalities in thiamine-dependent processes can be plausibly linked to the pathology of AD. Seemingly paradoxical properties of thiamine-dependent processes may underlie their relation to the pathophysiology of AD: Reduction of thiamine-dependent processes increase oxidative stress. Thiamine can act as a free radical scavenger. Thiamine-dependent mitochondrial dehydrogenase complexes produce oxygen free radicals and are sensitive to oxidative stress. Genetic disorders of thiamine metabolism that lead to neurological disease can be treated with large doses of thiamine. Although thiamine itself has not shown dramatic benefits in AD patients, the available data is scanty. Adding thiamine or more absorbable forms of thiamine to tested treatments for the abnormality in glucose metabolism in AD may increase their efficacy.

Gerontology. 1999; 45(2):96-101. Clinical relevance of thiamine status amongst hospitalized elderly patients. Pepersack T, Garbusinski J, Robberecht J, Beyer I, Willems D, Fuss M. Division of Geriatric Medicine, Brugmann University Hospital, Free University of Brussels, Belgium.

This article discusses the prevalence and the consequences of thiamine deficiency among elderly patients admitted to acute geriatric wards are not known. OBJECTIVES: (1) To assess the prevalence of thiamine deficiency in patients admitted to a geriatric ward compared to age-matched ambulatory outpatients; (2) to identify their diseases and problems associated with thiamine deficiency, and (3) to determine the relationship between the thiamine status and the cognitive and functional status of these patients. MATERIALS AND METHODS: 118 aged hospitalized patients (83+/−7 years; mean age+/−SD) were prospectively enrolled on admission to the geriatric ward. Their cognitive status was assessed using the Mini-Mental State Examination (MMSE) and their ability to perform their activities of daily living (ADL) using ADL scales. The effect of exogenous thiamine pyrophosphate (TPP) addition on the blood transketolase (TK) activity (TPP TK effect) served to estimate thiamine deficiency. Socioeconomic data, diseases and treatment were identified as potential associated risk factors. This group of hospitalized patients was divided according to their thiamine status to characterize the conditions associated with thiamine deficiency. Thirty-five outpatients without any functional or cognitive impairment served as a control group. RESULTS: Of 118 inpatients, 46 (39%) presented with a TPP TK effect of >15%, and 6 with values of >22%, indicating moderate and severe thiamine deficiency, respectively. Only 6 of 30 outpatients (20%) exhibited a TPP TK effect of >15% and none of them reached values of >18%. Although it tended to be lower in outpatients, the mean TPP TK effect did not statistically differ from the mean of inpatients. Thiamine-deficient inpatients comprised a larger proportion of institutionalized subjects than nondeficient inpatients (87 versus 47%, p<0.001). Functional status, cognitive functions and the occurrence of delirium did not differ according to their thiamine status. By contrast, thiamine-deficient inpatients exhibited a higher proportion of Alzheimer's disease, depression, cardiac failure and falls. Furosemide was more frequently taken by thiamine-deficient patients. CONCLUSIONS: Severe thiamine deficiency remained quite low among the hospitalized elderly. The prevalence of moderate thiamine deficiency approached 40%. Institutionalized subjects were at particular risk of developing thiamine deficiency. Its clinical relevance on functional status and on cognitive function remained not significant. By contrast, a high proportion of falls, Alzheimer's disease, depression, cardiac failure and furosemide use Alzheimer's Disease—Vitamin B6

Brain Nerve. 2007 July; 59(7):731-7. [Disruption of amino acid metabolism in astrocyte and neurological disorders—possible implication of abnormal glia-neuron network in homocystineuria] [Article in Japanese]. Enokido Y. Department of Neuropathology, Medical Research Institute, Tokyo Medical and Dental University, 1-5-45 Yushima, Bunkyo-ku, Tokyo 113-8519, Japan.

This article discusses CBS is a vitamin B6-dependent transsulfuration enzyme needed to synthesize cysteine from methionine, catalyzing the condensation of serine with homocysteine to form cystathionine. A deficiency of CBS causes homocystinuria (MIM 236200), one of the most prevalent inborn errors, characterized by mental retardation, seizures, psychiatric disturbances, skeletal abnormalities and vascular disorders. Patients with CBS deficiency exhibit a major biochemical abnormality, hyperhomocysteinemia (HHcy), a condition associated with highly elevated plasma homocysteine levels. HHcy is recognized as a risk factor for several neurological diseases, such as cognitive impairment, dementia and Alzheimer's disease. Although the link between CBS deficiency and homocystinuria was first described over 40 years ago and mental retardation was the first clinical feature of the disease to be classified, very little is known about the role of CBS in the CNS. Here we show the regional and cellular distribution of CBS in the adult and developing mouse brain. In the adult mouse brain, CBS was expressed ubiquitously, but most intensely in the cerebellar molecular layer and hippocampal dentate gyrus. Immunohistochemical analysis revealed that CBS is preferentially expressed in cerebellar Bergmann glia and in astrocytes throughout the brain. At early developmental stages, CBS was expressed in neuroepithelial cells in the ventricular zone, but its expression changed to radial glial cells and then to astrocytes during the late embryonic and neonatal periods. Moreover, CBS was significantly accumulated in reactive astrocytes in the hippocampus after kainic acid-induced seizures, and cerebellar morphological abnormalities were observed in CBS-deficient mice. These results support the role of CBS in the development and maintenance of the CNS, and suggest that radial glia/astrocyte dysfunction might be involved in the complex neuropathological features associated with abnormal homocysteine metabolism.

Nutr Hosp. 2007 January-February; 22(1):7-24, Vitamin B6 status, deficiency and its consequences—an overview. Spinneker A, Sola R, Lemmen V, Castillo M J, Pietrzik K, González-Gross M. Grupo Effects 262, Facultad de Medicina, Universidad de Granada, Spain.

This article discusses Vitamin B6 is thought to be a most versatile coenzyme that participates in more than 100 biochemical reactions. It is involved in amino acid and homocysteine metabolism, glucose and lipid metabolism, neurotransmitter production and DNA/RNA synthesis. Vitamin B6 can also be a modulator of gene expression. Nowadays, clinically evident vitamin B6 deficiency is not a common disorder, at least in the general population. Nevertheless, a subclinical, undiagnosed deficiency may be present in some subjects, particularly in the elderly. OBJECTIVE: This review gives a complete overview over the metabolism and interactions of vitamin B6. Further, we show which complications and deficiency symptoms can occur due to a lack of vitamin B6 and possibilities for public health and supplemental interventions. METHODS: The database Medline (www.ncvi.nlm.nih.gov) was searched for terms like "vitamin B6", "pyridoxal", "cancer", "homocysteine", etc. For a complete understanding, we included studies with early findings from the forties as well as recent results from 2006. These studies were summarised and compared in different chapters. RESULTS AND CONCLUSION: In fact, it has been proposed that suboptimal vitamin B6 status is associated with certain diseases that particularly afflict the elderly population: impaired cognitive function, Alzheimer's disease, cardiovascular disease, and different types of cancer. Some of these problems may be related to the elevated homocysteine concentrations associated to vitamin B6 deficiency, but there is also evidence for other mechanisms independent of homocysteine by which a suboptimal vitamin B6 status could increase the risk for these chronic diseases.

Cancer—Thiamine

South Med J. 2007 July; 100(7):717-9 Wernicke encephalopathy complicating lymphoma therapy: case report and literature review. Boniol S, Boyd M, Koreth R, Burton G V. Feist-Weiller Cancer Center, Louisiana State University Health Science Center, Shreveport, La. 71130, USA.

This article discusses Thiamine deficiency can occur in any disease that results in inadequate intake or excessive loss of vitamin B1. In addition to increased thiamine consumption secondary to high cell turnover, cancer patients frequently have reduced oral intake as a direct result of their cancer or from cancer treatments. However, Wernicke encephalopathy (cerebral Beriberi), a clinical manifestation of thiamine deficiency, has rarely been associated with cancer patients. We report a case of Wernicke encephalopathy in a nonalcoholic patient with lymphoma. Although thiamine deficiency rarely potentiates clinical sequelae in cancer patients, it is important to recognize the risk and the clinical signs and manifestations so that prompt therapy can be initiated to reverse morbidity.

Oncol Rep. 2007 April; 17(4):841-5. Transketolase protein TKTL1 overexpression: A potential biomarker and therapeutic target in breast cancer. Földi M, Stickeler E, Bau L, Kretz O, Watermann D, Gitsch G, Kayser G, Zur Hausen A, Coy J F. Department of Obstetrics and Gynaecology, University Hospital Freiburg, D-79106 Freiburg, Germany.

This article discusses malignant tumors degrade glucose to lactate even in the presence of oxygen via the pentose phosphate pathway (ppp). The non-oxidative part of the ppp is controlled by thiamine-dependant transketolase enzyme reactions. Overexpression of the transketolase-like-1-gene (TKTL1) in urothelial and colorectal cancer is associated with poor patient outcome. We analyzed the expression of the TKTL1 protein in a retrospective institution-based patient cohort with invasive breast cancer by immunohistochemical analysis of 124 paraffin-embedded breast cancer tissues. Our study revealed TKTL1 expression in 86% of breast cancer specimens with 45% showing high expression levels. In contrast, only 29% of corresponding non-neoplastic breast tissues were TKTL1 immunopositive, including 9% with high expression levels. High expression levels of TKTL1 correlated significantly to Her2/neu overexpression (p=0.015). However, TKTL1 expression failed to reach statistical significance for other common prognostic parameters. In contrast to recent data for e.g. colorectal cancer TKTL1 overexpression did not correlate to patient outcome and survival. However, in the context of novel insights into TKTL1-related tumor metabolism and the high proportion of TKTL1 overexpressing breast cancers, this enzyme represents a potential candidate for targeted inhibition of tumor growth in this tumor entity.

Oncol Rep. 2005 December; 14(6):1589-92. Thiamin deficiency: a possible major cause of some tumors? (review). Lee B Y, Yanamandra K, Bocchini J A Jr. Department of Pediatrics, Louisiana State University Health Sciences Center, 1501 Kings Hwy, Shreveport, La. 71130, USA. blee1@1suhsc.edu This article discusses that based solely on clinical clues from a malnourished population, thiamin alone was intentionally and successfully injected to human cases with some tumors or masses. Two cases of submandibular gland cyst and 13 out of 15 cases of Baker's cyst were cured without recurrence for several decades. In a case with pathology-confirmed osteosarcoma, subcutaneous perfusion of thiamin HCl 300 once only reduced its circumference from 30 to 20 cm, equivalent to a reduction of 50-75% in volume, within 2 days. Current concepts on the role of thiamin in carcinogenesis are controversial. Some authors claimed that thiamin supported high rate of tumor cell survival, proliferation and chemotherapy resistance and suggested anti-thiamin therapy for cancer. On the other hand, some investigators have reported evidence of prevention of several varieties of cancers by dietary thiamin. A limited number of animal studies revealed evident relationship between thiamin deficiency and cancer development. Therefore, further study on the mechanism switching thiamin between cancer supporter and suppressor is needed.

Cancer—Vitamin B6

J Nutr. 2007 July; 137(7):1808-14. Low intake of vitamin B-6 is associated with increased risk of colorectal cancer in Japanese men. Ishihara J, Otani T, Inoue M, Iwasaki M, Sasazuki S, Tsugane S; Japan Public Health Center-based Prospective Study Group.

This article covers Epidemiology and Prevention Division, Research Center for Cancer Prevention and Screening, National Cancer Center, 5-1-1 Tsukiji, Chuo-ku, Tokyo 104-0045, Japan. We investigated the association of dietary intakes of folate, vitamin B-6, vitamin B-12, and methionine with the risk of colorectal cancer in a large prospective cohort study of middle-aged Japanese men and women. A total of 81,184 subjects (38,107 men and 43,077 women) who participated in the Japan Public Health Center-based Prospective Study were followed from 1995-1998 to the end of 2002, during which 526 cases of colorectal cancer (335 men, 191 women) were newly identified. Dietary intake of nutrients was calculated using a 138-item self-administered FFQ. We observed a significant inverse association between vitamin B-6 intake and colorectal cancer in men. Compared with the lowest quartile, the multivariate hazard ratio (95% [CI]) in the highest quartile of intake was 0.69 (0.48-0.98) (P(trend) =0.03). Men who consumed 150 g/wk alcohol or more had twice the risk of colorectal cancer of those who drank less in the lowest quartile of vitamin B-6 intake, but risk due to alcohol intake was not higher in the highest quartile of vitamin B-6 intake. Vitamin B-6 intake and colorectal cancer were not associated in women. Folate and methionine intakes were not associated with colorectal cancer risk in men or women, but colorectal cancer risk tended to increase (P(trend)=0.05) with increasing intake of vitamin B-12 in men. Our results support previous evidence that low vitamin B-6 intake is associated with an increased risk of colorectal cancer. In particular, a higher intake of vitamin B-6 appears beneficial in men with higher alcohol intake.

Nutr Hosp. 2007 January-February; 22(1):7-24. Vitamin B6 status, deficiency and its consequences—an overview. Spinneker A, Sola R, Lemmen V, Castillo M J, Pietrzik K, González-Gross M. Grupo Effects 262, Facultad de Medicina, Universidad de Granada, Spain.

In this article Vitamin B6 is thought to be a most versatile coenzyme that participates in more than 100 biochemical reactions. It is involved in amino acid and homocysteine metabolism, glucose and lipid metabolism, neurotransmitter production and DNA/RNA synthesis. Vitamin B6 can also be a modulator of gene expression. Nowadays, clinically evident vitamin B6 deficiency is not a common disorder, at least in the general population. Nevertheless, a subclinical, undiagnosed deficiency may be present in some subjects, particularly in the elderly. OBJECTIVE: This review gives a complete overview over the metabolism and interactions of vitamin B6. Further, we show which complications and deficiency symptoms can occur due to a lack of vitamin B6 and possibilities for public health and supplemental interventions. METHODS: The database Medline (www.ncvi.nlm.nih.gov) was searched for terms like "vitamin B6", "pyridoxal", "cancer", "homocysteine", etc. For a complete understanding, we included studies with early findings from the forties as well as recent results from 2006. These studies were summarised and compared in different chapters. RESULTS AND CONCLUSION: In fact, it has been proposed that suboptimal vitamin B6 status is associated with certain diseases that particularly afflict the elderly population: impaired cognitive function, Alzheimer's disease, cardiovascular disease, and different types of cancer. Some of these problems may be related to the elevated homocysteine concentrations associated to vitamin B6 deficiency, but there is also evidence for other mechanisms independent of homocysteine by which a suboptimal vitamin B6 status could increase the risk for these chronic diseases.

Curr Opin Investig Drugs. 2006 October; 7(10):912-5. Vitamins: not just for enzymes. Bolander F F. University of South Carolina, Department of Biological Sciences, Columbia, S.C. 29208, USA. bolander@sc.edu This article describes that vitamins have traditionally played the role of coenzymes, organic molecules that facilitate the chemical reactions catalyzed by enzymes. However, several vitamins assume additional endocrine-like actions; this review will discuss four such vitamins. Vitamin K2 is involved in the gamma-carboxylation of coagulation factors and bone proteins, but it can also bind and activate the steroid and xenobiotic receptor in order to mediate transcription in bone tissue, and has been used to treat osteoporosis. Biotin is critical for some carboxylation reactions, but it also induces epidermal differentiation and has been used to treat lameness in animals and brittle nails in humans. Pyridoxal phosphate (the active form of vitamin B6) is involved in a multitude of reactions, including decarboxylation and transamination; it can also inhibit DNA polymerases and several steroid receptors and may prove useful as an adjunct in cancer chemotherapy. Finally, nicotinic acid is converted to NAD+ and NADP+, which are used as hydrogen/electron carriers in redox.

Use of the Supplement Composition for Sports Participants

As a general rule if one is going to engage in a strenuous activity that would normally result in muscle pain and inflammation we suggest that you take 2 capsules of the novel composition approximately 30 to approximately 60 minutes before a run, workout or participation in any sports activity. This gives the supplement nutrients time to get into your blood stream. The benefits of the novel composition are usually noticeable within approximately 30 to approximately 60 minutes of taking the composition. It is also suggested that upon completion of the activity the user take approximately 2 more capsules of the novel composition. With this regimen the user should find their stamina and endurance increasing while the aftereffects of their strenuous physical activity are dramatically decreasing. The dosages can be reduced or increased as desired and by experimenting with various dosage regimens.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A composition for treating pain and inflammation associated with joint discomfort and muscle strains, and for treating stiffness and discomfort related to bumps and bruises, the composition consisting of:

Vitamin B1;
Vitamin B6;
Curcumin;
*Boswellia Serrata* herb extract;
Quercetin;
D,L-Phenylalanine; and
Bromelain.

2. A dietary supplement, consisting of:
approximately 25 mg of Vitamin B1;
approximately 25 mg of Vitamin B6;
approximately 200 mg of Curcumin;
approximately 175 mg of *Boswellia Serrata* herb extract;
approximately 75 mg of Quercetin;
approximately 75 mg of D,L-Phenylalanine; and
approximately 125 mg of Bromelain.

3. A dietary supplement, consisting of:
two capsules, each of the capsules consisting of:
    approximately 25 mg of Vitamin B1;
    approximately 25 mg of Vitamin B6;
    approximately 200 mg of Curcumin;
    approximately 175 mg of *Boswellia Serrata* herb extract;
    approximately 75 mg of Quercetin;
    approximately 75 mg of D,L-Phenylalanine; and
    approximately 125 mg of Bromelain.

4. The composition of claim 1, wherein the composition includes:
approximately 25 mg of said Vitamin B1;
approximately 25 mg of said Vitamin B6;
approximately 200 mg of said Curcumin;
approximately 175 mg of said *Boswellia Serrata* herb extract;
approximately 75 mg of said Quercetin;
approximately 75 mg of said D,L-Phenylalanine; and
approximately 125 mg of said Bromelain.

* * * * *